United States Patent
Romero et al.

(10) Patent No.: US 9,603,984 B2
(45) Date of Patent: Mar. 28, 2017

(54) TRIPLE HELIX DRIVELINE CABLE AND METHODS OF ASSEMBLY AND USE

(71) Applicant: Thoratec Corporation, Pleasanton, CA (US)

(72) Inventors: Jaime Romero, San Leandro, CA (US); Nathan Harold, Pleasanton, CA (US)

(73) Assignee: TCI LLC, St. Paul, MN (US)

( * ) Notice: Subject to any disclaimer, the term of this patent is extended or adjusted under 35 U.S.C. 154(b) by 0 days.

(21) Appl. No.: 14/844,567

(22) Filed: Sep. 3, 2015

(65) Prior Publication Data
US 2016/0064117 A1 Mar. 3, 2016

Related U.S. Application Data (60) Provisional application No. 62/045,365, filed on Sep. 3, 2014.

(51) Int. Cl.
*A61N 1/362* (2006.01)
*A61M 1/12* (2006.01)
(Continued)

(52) U.S. Cl.
CPC ............. *A61M 1/127* (2013.01); *H01B 1/026* (2013.01); *H01B 7/048* (2013.01); *A61M 1/122* (2014.02); *A61M 2205/04* (2013.01)

(58) Field of Classification Search
CPC .. A61M 1/122; A61M 1/127; A61M 2205/04; H01B 1/026; H01B 7/048; C07K 14/22
See application file for complete search history.

(56) References Cited

U.S. PATENT DOCUMENTS

| 5,695,471 A | 12/1997 | Wampler |
| 5,888,242 A | 3/1999 | Antaki et al. |

(Continued)

FOREIGN PATENT DOCUMENTS

| GB | 1080844 | 8/1967 |
| WO | 0146737 | 6/2001 |
| WO | 2010042006 | 4/2010 |

OTHER PUBLICATIONS

Litz Types and Construction. [online]. New England Wire Technologies, 2008 [retrieved on Aug. 6, 2016]. Retrieved from the Internet: <URL: http://www.litzwire.com/litz_types.htm>.
(Continued)

*Primary Examiner* — George Manuel
(74) *Attorney, Agent, or Firm* — Kilpatrick Townsend & Stockton LLP (57) ABSTRACT

A power cable having improved durability and associated methods of assembly and use are described herein. In one aspect, the power cable is adapted for use in powering an implantable circulatory pump system. The cable includes one or more conductors of uninsulated wire strands that are loosely packed so as to move relative one another during cable flexure. The driveline cable may include a plurality of conductors, each comprised of multiple uninsulated bundles of uninsulated, loosely packed wire strands of a conductive material, that are wrapped about a central core. The cable may include at least six conductors, each conductor having at least 200 wire strands of a 30 gauge or higher. The cable may include the plurality of wire strands wound in a Litz style configuration to provide improved durability over many cycles of use at reduced cost, improved integrity of the electrical connection and reduced diameter.

26 Claims, 10 Drawing Sheets

(51) Int. Cl.
*H01B 1/02* (2006.01)
*H01B 7/04* (2006.01)

(56) References Cited

U.S. PATENT DOCUMENTS

| | | | |
|---|---|---|---|
| 6,071,093 | A | 6/2000 | Hart |
| 6,116,862 | A | 9/2000 | Rau et al. |
| 6,186,665 | B1 | 2/2001 | Maher et al. |
| 6,234,772 | B1 | 5/2001 | Wampler et al. |
| 6,264,635 | B1 | 7/2001 | Wampler et al. |
| 6,672,894 | B2 | 1/2004 | Sprunger et al. |
| 6,688,861 | B2 | 2/2004 | Wampler |
| 6,991,595 | B2 | 1/2006 | Burke et al. |
| 7,271,340 | B2 | 9/2007 | Buck et al. |
| 7,504,588 | B2 | 3/2009 | Robberding et al. |
| 7,699,586 | B2 | 4/2010 | LaRose et al. |
| 7,706,424 | B2 | 4/2010 | Amada et al. |
| 7,976,271 | B2 | 7/2011 | LaRose et al. |
| 7,997,854 | B2 | 8/2011 | LaRose et al. |
| 8,007,254 | B2 | 8/2011 | Marquis et al. |
| 8,152,493 | B2 | 4/2012 | Thyagarajan et al. |
| 8,323,174 | B2 | 12/2012 | Jeevanandam et al. |
| 8,382,830 | B2 | 2/2013 | Maher et al. |
| 8,449,444 | B2 | 5/2013 | Poirier et al. |
| 8,506,471 | B2 | 8/2013 | Bourque |
| 8,562,508 | B2 | 10/2013 | Dague et al. |
| 8,597,350 | B2 | 12/2013 | Rudser et al. |
| 8,652,024 | B1 | 2/2014 | Yanai et al. |
| 8,657,733 | B2 | 2/2014 | Ayre et al. |
| 8,668,473 | B2 | 3/2014 | Marquis et al. |
| 8,668,526 | B2 | 3/2014 | Cotter |
| 8,682,431 | B2 | 3/2014 | Callaway et al. |
| 8,692,170 | B2 | 4/2014 | Parsche et al. |
| 2002/0129969 | A1 | 9/2002 | Groegl et al. |
| 2005/0071001 | A1 | 3/2005 | Jarvik |
| 2005/0213783 | A1* | 9/2005 | Walsh ............... H03F 3/181 381/120 |
| 2007/0078293 | A1 | 4/2007 | Shambaugh et al. |
| 2007/0255089 | A1* | 11/2007 | Vincent ............... A61M 1/1053 600/17 |
| 2007/0270314 | A1 | 11/2007 | Huang et al. |
| 2008/0021394 | A1 | 1/2008 | LaRose et al. |
| 2009/0203957 | A1 | 8/2009 | LaRose et al. |
| 2009/0295531 | A1 | 12/2009 | Silva et al. |
| 2012/0046514 | A1 | 2/2012 | Bourque |
| 2012/0095281 | A1 | 4/2012 | Reichenbach et al. |
| 2012/0149229 | A1 | 6/2012 | Kearsley et al. |
| 2013/0014973 | A1 | 1/2013 | Shinmoto et al. |
| 2013/0096364 | A1 | 4/2013 | Reichenbach et al. |
| 2013/0121821 | A1 | 5/2013 | Ozaki et al. |
| 2013/0127253 | A1 | 5/2013 | Stark et al. |
| 2013/0170970 | A1 | 7/2013 | Ozaki et al. |
| 2013/0225909 | A1 | 8/2013 | Dormanen et al. |
| 2013/0310629 | A1 | 11/2013 | Lafontaine et al. |
| 2013/0314047 | A1 | 11/2013 | Eagle et al. |
| 2014/0288352 | A1* | 9/2014 | Yanai ............... A61M 1/122 600/16 |

OTHER PUBLICATIONS

Litz Wire. [online]. Wikipedia [retrieved on Aug. 6, 2016]. Retrieved from the Internet: <URL: http://en.wikipedia.org/wiki/Litz_wire>.

Product Selection Guide. [online] New England Wire Technologies, 2005 [retrieved on Aug. 29, 2016]. Retrieved from the Internet: <URL: https://www.newenglandwire.com/newt-catalog.pdf>.

* cited by examiner

TRIPLE HELIX DRIVELINE CABLE AND METHODS OF ASSEMBLY AND USE

REFERENCES TO RELATED APPLICATIONS

This application is a Non-Provisional of and claims the benefit of priority of U.S. Provisional Application No. 62/045,365 filed on Sep. 3, 2014, the entire contents of which are incorporated herein by reference.

BACKGROUND OF THE INVENTION

This application relates generally to power cables, and particularly to power cables for low frequency AC and DC applications, such as may be used for a driveline cable to power implantable mechanical circulatory support systems.

Ventricular assist devices, known as VADs, are implantable blood pumps used for both short-term (i.e., hours, days, months) and long-term applications (i.e., years or a lifetime) where a patient's heart is incapable of providing adequate circulation, for example, due to heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body through a driveline cable. The driveline cable can also be configured for data communication and control functions.

Since loss of power of an implanted VAD or failure to recharge an associated power supply poses life threatening consequences, to ensure continuous operation of the VAD, the driveline cable must provide a dependable electrical connection. Because the driveline cable may be subjected to movement or flexure over the course of its lifetime after implantation of the system, it is desirable if such driveline cables can withstand many cycles of use while maintaining integrity of the electrical connection. To provide such features, driveline cables often utilize high cost materials, such as drawn filled tubing wire and metal-to-metal composites, and may have a form factor (e.g., sizable diameter or shape) that require larger tunnels through tissues when implanted and/or larger incisions when percutaneously placed. It would be desirable to provide driveline power cables having improved durability at reduced cost of manufacture and reduced dimensions (e.g., diameter or shape), while maintaining the electrical and mechanical integrity of the power cable.

BRIEF SUMMARY OF THE INVENTION

The invention relates generally to power cables, and in one embodiment, to a driveline cable for powering a mechanical circulatory support system, such as a VAD. Such cables may be used in various differing types of mechanical circulatory support systems and may be suitable for drivelines implanted entirely within the body, percutaneous driveline cables that extend outside the body through an incision in the skin, or an external modular driveline. In certain aspects, the invention allows for power cables suitable for powering any electrical device, implantable or otherwise in a direct current (DC) or low frequency alternating current (AC) application.

In one aspect, a cable in accordance with aspects of the invention includes multiple conductors, each conductor comprising multiple loosely packed uninsulated wire strands disposed within an outer insulating layer, the plurality of conductors being wound along a longitudinal axis of the cable and an outer jacket disposed about the wound plurality of conductors. The plurality of wire strands of each conductor may be formed of any suitable conducting material, such as a copper alloy, the wire strands being wound along an axis of the respective conductor. Typically, a loosely packed strand configuration is an arrangement where wire strands have a high degree of movement relative to each other, yet there is minimal space among the strands. This maximizes the packing factor of strands, or the maximum number of strands that can be placed into a given conductor diameter. Loosely packed strands move with respect to each other when the conductor or cable is manipulated. The limited space among the strands means the wound cable will maintain its cross-sectional shape during manipulation. The wire strands may be assembled in a configuration loosely similar to a Litz wire configuration but distinguishable in various aspects. Among these distinguishable aspects is that the wire strands are uninsulated. In some embodiments, the cable may include six or more conductors wound about a central core strength member extending along the length of the cable. In certain embodiments, each conductor includes at least 60 wire strands of 30 gauge or higher, such as 200 wire strands or more of gauge 40 or higher, preferably 288 strands of 50 gauge wire.

In one aspect, the cable includes conductors formed of multiple uninsulated wire strands that are loosely packed and assembled in a triple-helix configuration formed by three sequential winding operations in which the wire strands are wound along three distinct axes. For example, the wire strands may be wound in a first winding pattern to form multiple uninsulated bunches that are wound in a second winding pattern to form bundles of bunches, after which multiple bundles are wound in a third winding pattern to form the conductor. The multiple insulated conductors are then wound in a fourth pattern to form the cable. The conductors may be wound around a central core, such as a polymer member, to provide additional strength to the cable. The fourth winding pattern may including winding the conductors at 0.75 inch pitch or less along the longitudinal axis of the cable, such as a 0.6 inch pitch, so as to provide a spring-like effect that further reduces stresses and improves durability of the cable.

In another aspect, the invention provides methods of assembling a power cable, such as a driveline cable for an implantable ventricular assist device. Such methods may include: winding a plurality of uninsulated wire strands to form multiple bunches, each bunch comprising loosely packed uninsulated wire strands wound in a first pattern along a longitudinal axis of the respective bunch; winding the plurality of bunches to form multiple bundles, each bundle comprising multiple bunches of the plurality wound in a second pattern along a longitudinal axis of the respective bundle; and winding the multiple bundles in a third pattern to form a plurality of conductors; covering each of the plurality of conductors with an insulating layer; winding the conductors together in a fourth pattern along a longitudinal axis of the cable; and covering the wound conductors with an outer jacket. The configuration of the first, second and third winding patterns may correspond to patterns loosely similar to those used in a Litz wire configuration, and notably uses wire strands that are uninsulated. In certain embodiments, the uninsulated wire strands are 30 gauge or higher and each bundle includes 60 or more wire strands, such that a conductor includes 200 or more wire strands, such as 288 strands of a copper alloy of 50 gauge wire.

In another aspect, the invention provides a method of powering a device using a cable assembled in accordance with aspects of the invention. Such methods may include: electrically connecting a power cable to a device, wherein the power cable comprises: multiple conductors, each conductor comprising multiple loosely packed uninsulated wire strands, and an outer jacket covering the power cable; and powering the device using a low frequency AC, such as about 20 kHz or less, or DC transmitted through the power cable. Such methods include use of a cable formed according to any aspects of the invention described herein, such as a cable having multiple uninsulated wire strands that are loosely packed, including such strands wound according to any of the configurations described herein.

DETAILED DESCRIPTION OF THE INVENTION

The invention relates generally to power cables, and in one embodiment, to a driveline cable for powering a mechanical circulatory support system, such as VAD. Various aspects of the invention are similar to those described in U.S. Pat. No. 8,562,508 entitled "Mobility-Enhancing Blood Pump System," filed Dec. 30, 2009; U.S. Application Publication No. 2012/0149229 entitled "Modular Driveline," published on Jun. 14, 2012; and U.S. Pat. No. 8,682,431 entitled "Driveline Cable Assembly," filed Jan. 23, 2013; each of which the entire contents are incorporated herein by reference for all purposes.

Figure 1A:
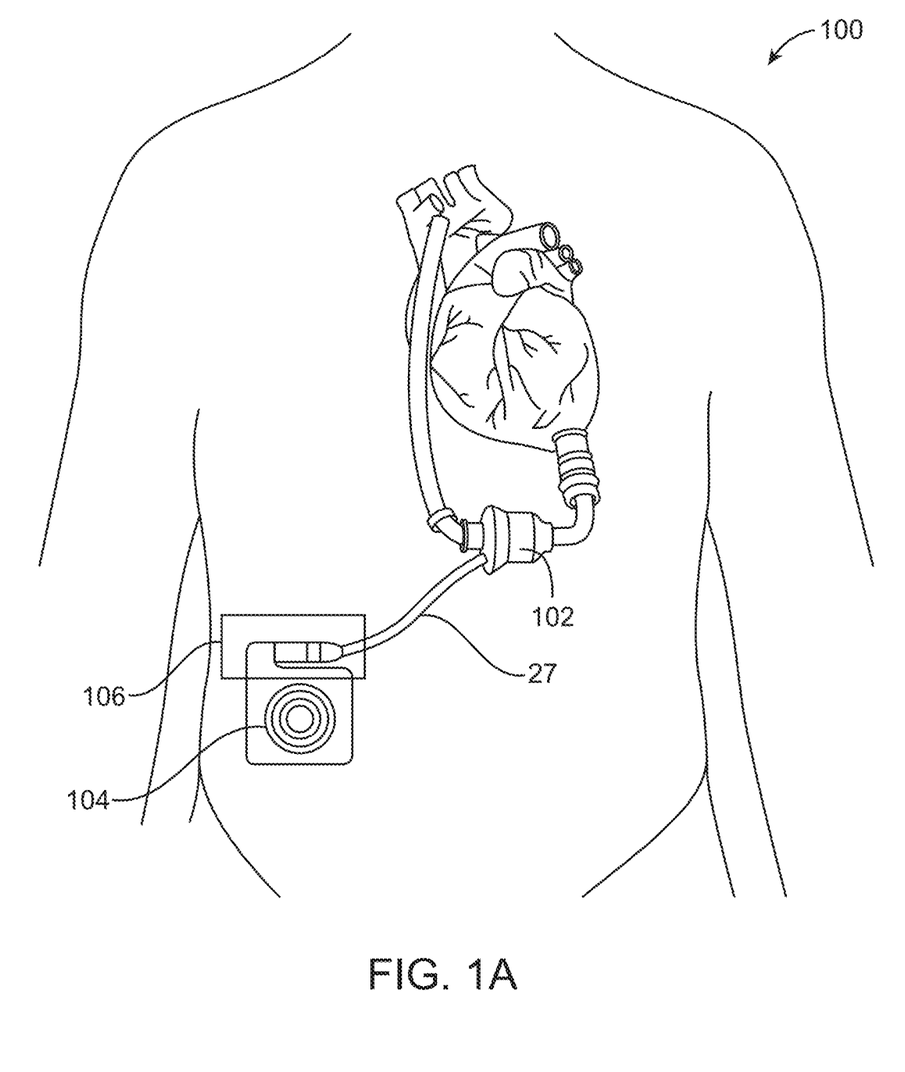
FIG. 1A is an illustration of a mechanical circulatory support system fully implanted in a patient's body with an associated driveline in accordance with aspects of the invention.

FIG. 1A illustrates an medical system 100 that includes an implantable medical device 102, shown as a VAD, and an implanted module 104 configured to receive wireless power from outside the body to provide power for the medical device. A bulkhead connector 106 and drive line cable 27 connect the implanted module to the medical device to provide power, data, and or/control signals from the module to the device. Such medical devices may be relatively high powered devices. In one aspect, the implanted module is configured to remain inside the patient's body for a minimum of two years and to serve as the power source and controller for the medical device. The module can supply ~16 V AC to drive the medical device and may be used to provide voltages as low as 10 V or as high as 24 V if needed. The clinician can surgically replace the implanted module by disconnecting the existing driveline cable from the existing module, removing the existing module, and reconnecting the same driveline cable to a new module without removing the medical device. Similarly, a clinician can surgically replace the cable and/or medical device while leaving the implanted module in place.

Figure 1B:
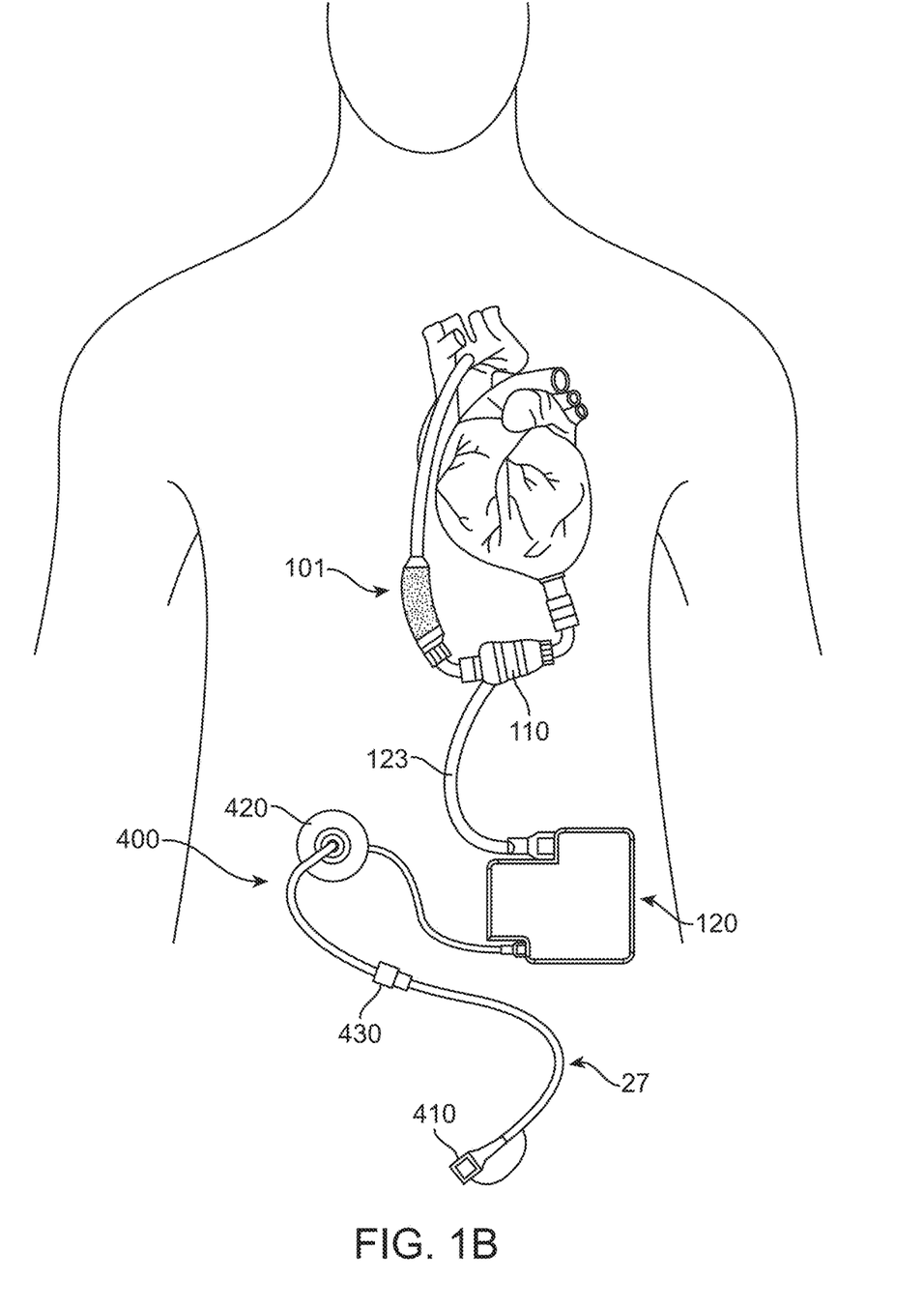
FIG. 1B is an illustration of a mechanical circulatory support system implanted in a patient's body with a modular driveline in accordance with aspects of the invention.

FIG. 1B illustrates a modular implanted ventricular assist device including an internal blood pump assembly 110, an internal controller assembly 120 connected to the blood pump assembly via an electrical conduit 123, internal rechargeable power storage device contained within the controller assembly 120, and a percutaneous lead 400 connected to the controller assembly 120 and exiting the body at an aperture port 420. The power storage device may include one or more "smart" lithium-chemistry batteries that are readily rechargeable. The distal end of driveline cable 27 includes a connector 410 for connection to an external power source for periodic charging of the internal power storage device of controller assembly 120. The percutaneous lead may connect to a driveline cable 27 at connector 430 such that the driveline cable can be removed and replaced as needed.

The blood pump 110 can be a VAD, which is a mechanical circulatory device that is used to partially or completely replace the function of a failing heart. Some VADs are intended for short term use, typically for patients recovering from heart attacks or heart surgery, while others are intended for long term use (e.g., years, and the remainder of a user's life), typically for patients suffering from congestive heart failure. VADs are designed to assist either the right (RVAD) or left (LVAD) ventricle, or both at once (BiVAD). VADs can be designed with an axial flow or centrifugal flow configuration. The impeller may be suspended by journal bearing such as a ball and cup, or by magnetic or hydrodynamic forces or both. In other embodiments, the blood pump can be an artificial heart, which is designed to completely take over cardiac function and may require the removal of a patient's heart. It should be appreciated that the technical features disclosed herein apply equally to any variation of the blood pump as described in this disclosure.

Figure 1C:
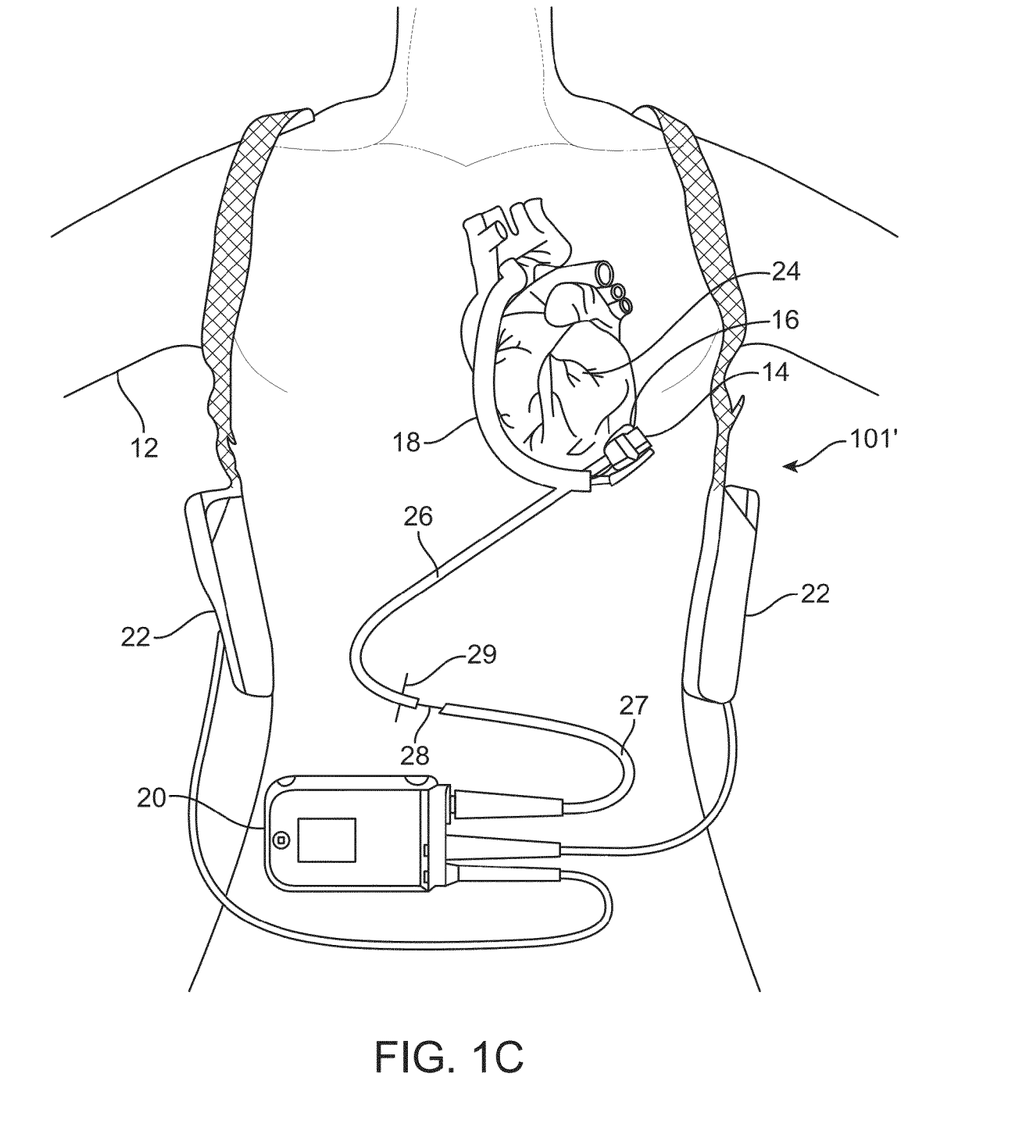
FIG. 1C is an illustration of an alternative implanted mechanical circulatory support system with a modular driveline in accordance with aspects of the invention.

FIG. 1C is an alternative set-up of an exemplary implanted mechanical circulatory support system 101' implanted in a patient's body 12 which may be powered with a driveline cable 27 in accordance with the present invention. The mechanical circulatory support system 101' comprises an implantable blood pump 14, ventricular cuff 16, outflow cannula 18, system controller 20, and power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. The blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1C illustrates the exemplary mechanical circulatory support system 101' during battery 22 powered operation. The percutaneous cable 26 connects the implanted blood pump 14 to the system controller 20 through driveline cable 27. The percutaneous cable 26 exits the patient's abdomen at aperture 29 and connects to the driveline at modular connection 28. The system controller 20 monitors system operations. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by one, two, or more batteries 22. It will be appreciated that although the system controller 20 and power source 22 are illustrated outside/external to the patient body, the driveline cable 27, system controller 20 and/or power source 22 may be partially or fully implantable within the patient, as separate components or integrated with the blood bump 14. Examples of such modifications are further described in U.S. Pat. No. 8,562,508 and U.S. Patent Publication No. 2013/0127253, all of which are incorporated herein by reference for all purposes in their entirety.

Implantable medical pumps, such as those described above and shown in FIGS. 1A-1C, are used to provide mechanical assistance or augmentation to pumping performed by the left and/or right ventricles of the heart. Due to the pumping volume and constant operation required in such application, such pumps typically have substantial power requirements, often necessitating a remotely located power source, usually an external power source worn outside the body, such as shown in FIG. 1C. Such pump systems are typically powered through a driveline cable 27, which may be implanted fully or partly, or may be entirely outside the patient. Since the driveline is subject to frequent movement and flexure, the drivelines cables must be able to withstand many cycles of use without failure. Failure typically includes a compromised electrical connection due to breakage of the conductors due to repeated stresses on the wire strands during flexure of the cable. It is further appreciated that a cable in accordance with aspects of the invention may be used in various other applications apart from implantable heart pumps. For example, the driveline cable may be used to transmit power to any number of devices from a power source in various DC or low frequency AC application and provide the advantages described herein.

The invention provides a configuration having improved durability at reduced cost of materials and production, improved electrical integrity and/or reduced diameter as compared to conventional designs. In one aspect, the configuration entails a cable having one or more conductors of multiple uninsulated wire strands in a loosely packed bundle. The loosely packed nature of the wire strands in each bundle allows the wire strands to move or slide relative to other wire strands during flexure of the cable, which allows for flexibility of the cable while reducing strain that would otherwise result in breakage of one or more wire strands.

By utilizing uninsulated wire strands, the configuration further allows for improved integrity because the cable is essentially self-healing. For example, if one or more wire strands break, the electrical connectivity of the cable is not compromised because the current can still transmitted by adjacent uninsulated wire strands. Conventional cables formed of Litz wires require the individual wires to be insulated to reduce skin effect and proximity effect losses. In cables utilizing multiple insulated wire strands, such as used in conventional Litz wire, breakage of one or more such wire strands compromises the integrity of the electrical connection since the insulation prevents current from traveling through the broken wire strands, which further limits the lifetime of such cables. Although conventional VAD driveline cables may utilize conductors having uninsulated wire strands, such conventional cables lack the improved durability and advantages of the driveline cable as described herein.

In one aspect, a cable configuration in accordance with the invention includes multiple conductors, each conductor including multiple uninsulated bunches of insulated wire strands wound together. The wire strands may be of any suitable conductive material, such as aluminum, copper or any suitable alloys, such as copper-cadmium. In some embodiments, the individual conductors are insulated and wound about a central core material, such as a polymer based strength member, that provides additional strength to the cable. The conductors may be covered with an insulating coating. The entire assembly may be covered with a shield and/or a polymer based wrap. Additional layers may be used to provide electrical shielding or protection or strength to the cable, such layers may include a suitable metallic shield or polymer covering, respectively.

Figure 2:
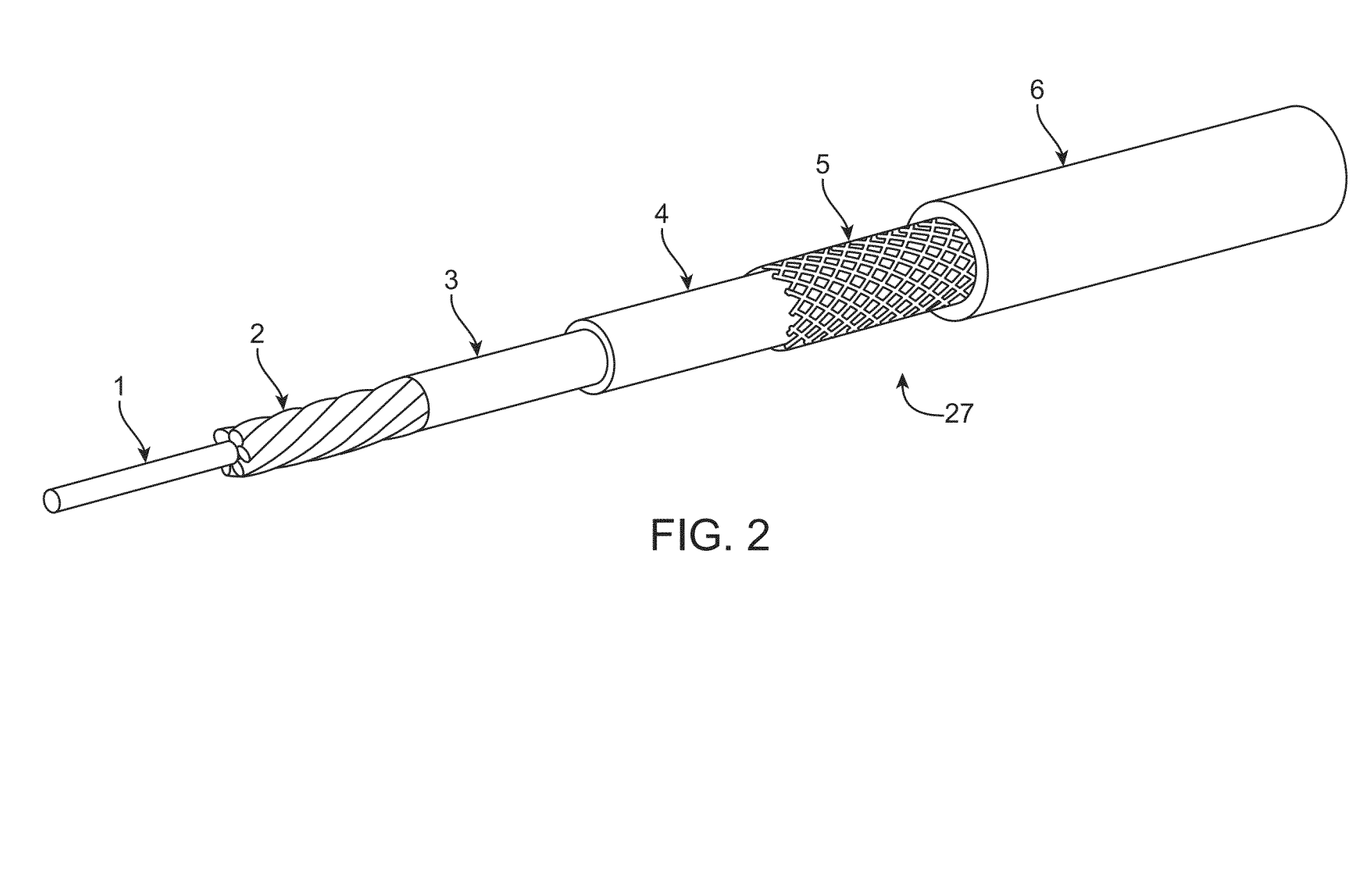
FIG. 2 is an illustration of an example driveline cable in accordance with aspects of the invention.
Figure 3:
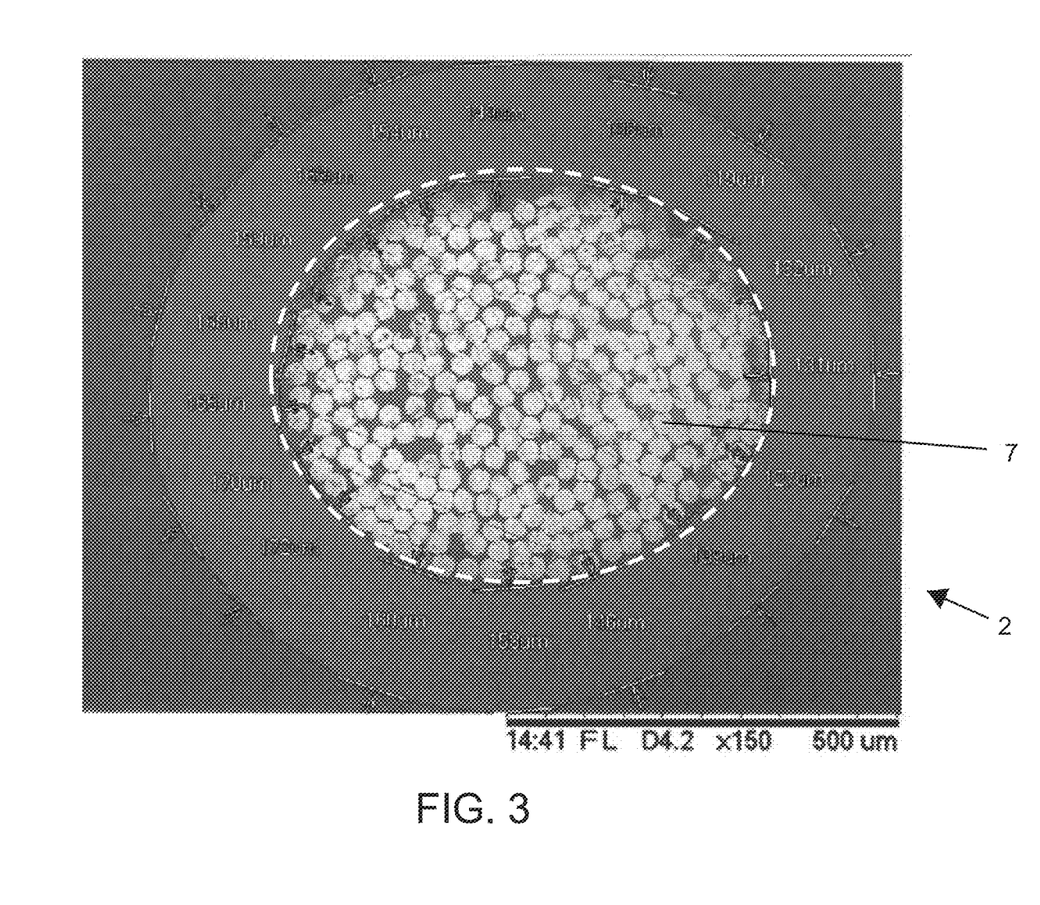
FIG. 3 is a cross-section of a conductor for use in a driveline cable in accordance with aspects of the invention.

In the example embodiment shown in FIG. 2, the driveline cable 27 includes a central core 1 around which insulated conductors 2 are wound, each conductor comprising uninsulated wire strands of a that are loosely packed. In the exemplary embodiment, the cable is configured to power a VAD with a three-phase motor. The exemplary cable includes a redundant set of wires, and accordingly, includes a total of six insulated conductors 2. The insulated conductors may be formed of copper alloy or other suitable material. The central core 1 may be a polyethylene strength member and the conductors 2 may be wound at a 1.00 inch pitch or less, preferably a 0.75 pitch or less, such as at a 0.6 inch pitch. Advantageously, the configuration of the conductors allows for tighter wrapping at smaller, tighter pitches that creates a spring-like effect which considerably reduces strain forces and further improves durability. The wound conductors 2 may be surrounded by a polytetrafluoroetheylene (PTFE) layer 3, followed by a polymer layer with moisture ingress resistance properties 4, such as a Bionate®, a PCU (thermoplastic polycarbonate-urethane) layer, followed by an aramid armor layer 5, and an outer silicone jacket 6. Each of the conductors is comprised of loosely packed uninsulated wire strands, typically uninsulated bunches of loosely packed uninsulated wire strands that are wound together. In the exemplary embodiment shown in FIG. 2, each of the six insulated conductors includes 288 uninsulated copper alloy strands wound in unwrapped bundles. As shown in FIG. 3, the resulting voids between wire strands are greatly reduced as compared to conventional VAD cable designs.

Figure 4:
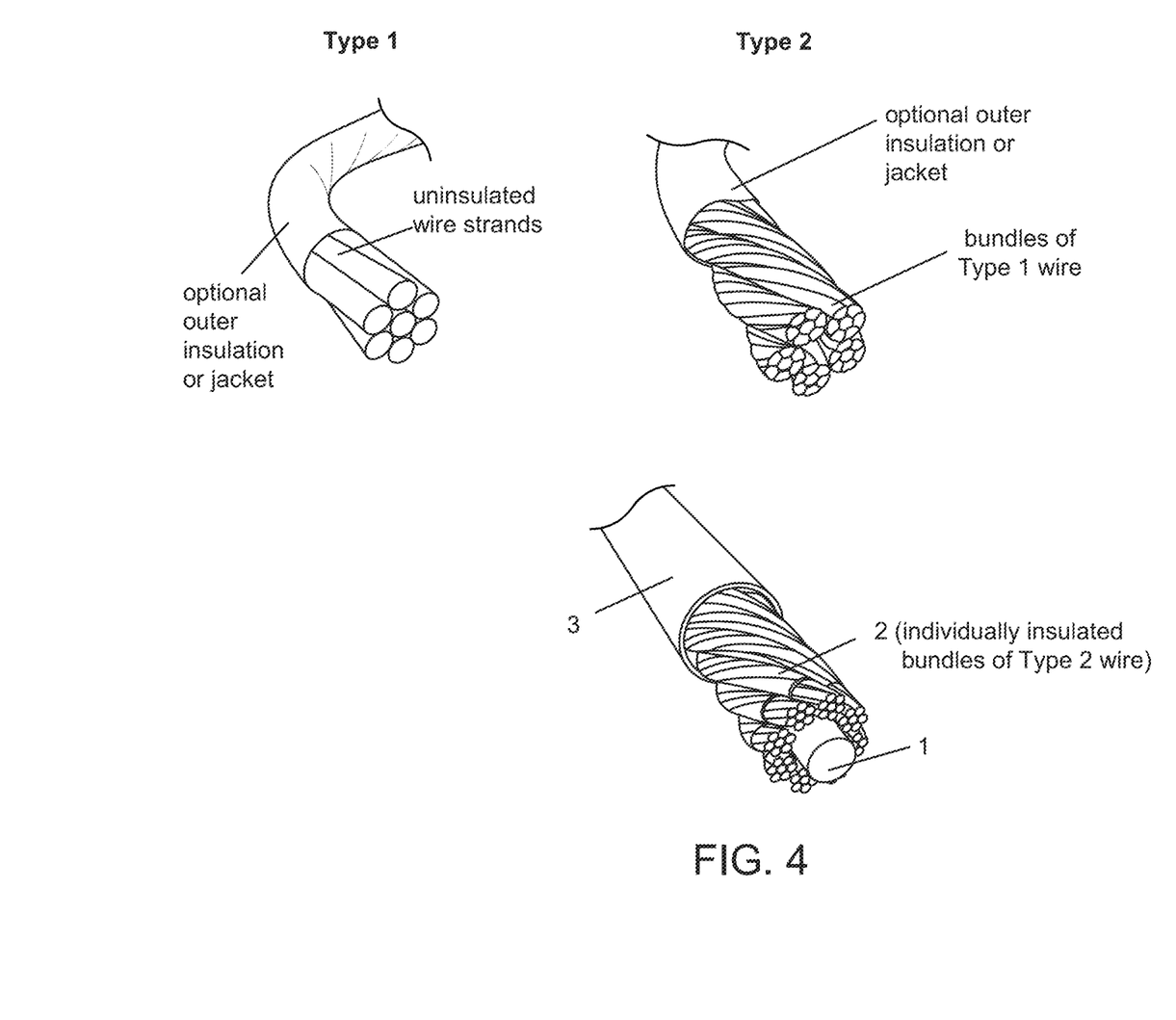
FIG. 4 illustrates various types of winding patterns applicable to fabrication of a driveline cable in accordance with aspects of the invention.

In one aspect, the exemplary cable comprises uninsulated wire strands wound in a triple-helix configuration defined by three sequential cabling/twisting operations. Such winding of bundles allows production of high strand count conductors. It has been found that winding wire strands of 30 gauge or higher becomes problematic when more than about 60 wire strands are wound at one time. Therefore, to allow for high strand conductors, the configuration and methods described herein utilize multiple bunches of less than 60 wire strands of 30 gauge or higher that are wound together. In some embodiments, individual, uninsulated wire strands are wound together in a first pattern to form uninsulated bunches of wire strands, the resulting bunches being wound together in a second pattern to form multiple bundles, which are wound together in a third pattern to form individual conductors. The individual conductors may be wrapped with an insulative coating and then wrapped in a fourth pattern to form the final cable configuration. Each of the first, second and third patterns may consist of a twisting that is substantially uniform along the respective longitudinal axis. These configuration and cabling operations may utilize winding patterns loosely similar to those used for Litz wires, which in stark contrast to the present cable, utilize insulated wire strands (see, e.g., FIG. 5B). Examples of various winding patterns that may be used for the first, second and third patterns are shown in FIG. 4. Although in some aspects, these winding patterns may be somewhat similar to twisting patterns or arrangements used for Litz wire, it is appreciated that the cable is not limited to any particular Litz wire configuration, nor do the embodiments described herein correspond in pattern or arrangement to any particular known Litz wire configuration.

FIG. 3 illustrates a cross-section of a conductor 2 formed in accordance with the embodiment described above to include multiple bunches of uninsulated wire strands 7 that are loosely-packed, meaning that a majority of the individual wire strands are free to move relative to other wire strands of the bunch when the cable is flexed. By providing uninsulated wire strands that are loosely-packed, the friction between adjacent wire strands is reduced and the wire strands are allowed more freedom of movement such that during twisting the voids between bundles are substantially reduced (as shown in FIG. 3, the individual bundles are no longer readily apparent since the voids between bundles are largely eliminated). FIG. 3 illustrates a conductor having a 3×3×32/50 design, which is three bundles of 50 gauge wire strands, each bundle comprising three bunches wound together, each bunch having 32 wire strands so that the conductor includes 288 total wire strands. The greater freedom of movement of each wire strand in the conductors reduces strain in the wire strands during bending and further allows for reduced conductor diameter. As would be understood by one of skill in the art, even small reductions in voids within the cable allows for a smaller pitch winding with the same diameter as existing cable. The above configuration also allows for a smaller pitch wrapping of conductors in the cable, which further reduces strain of the conductors during bending. The combined freedom of movement and smaller pitch wrapping has demonstrated substantially improved durability over drivelines with conventional conductors.

Figure 5A:
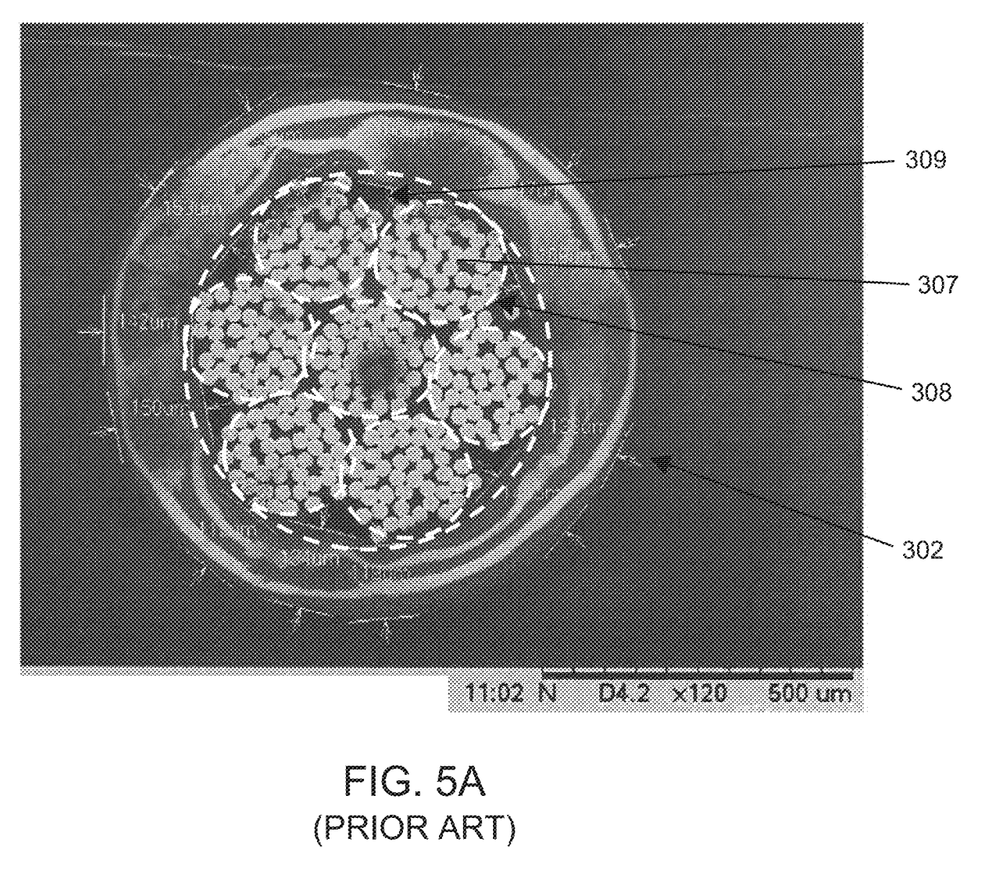
FIG. 5A is a cross-section of a conductor in a conventional driveline cable.
Figure 5B:
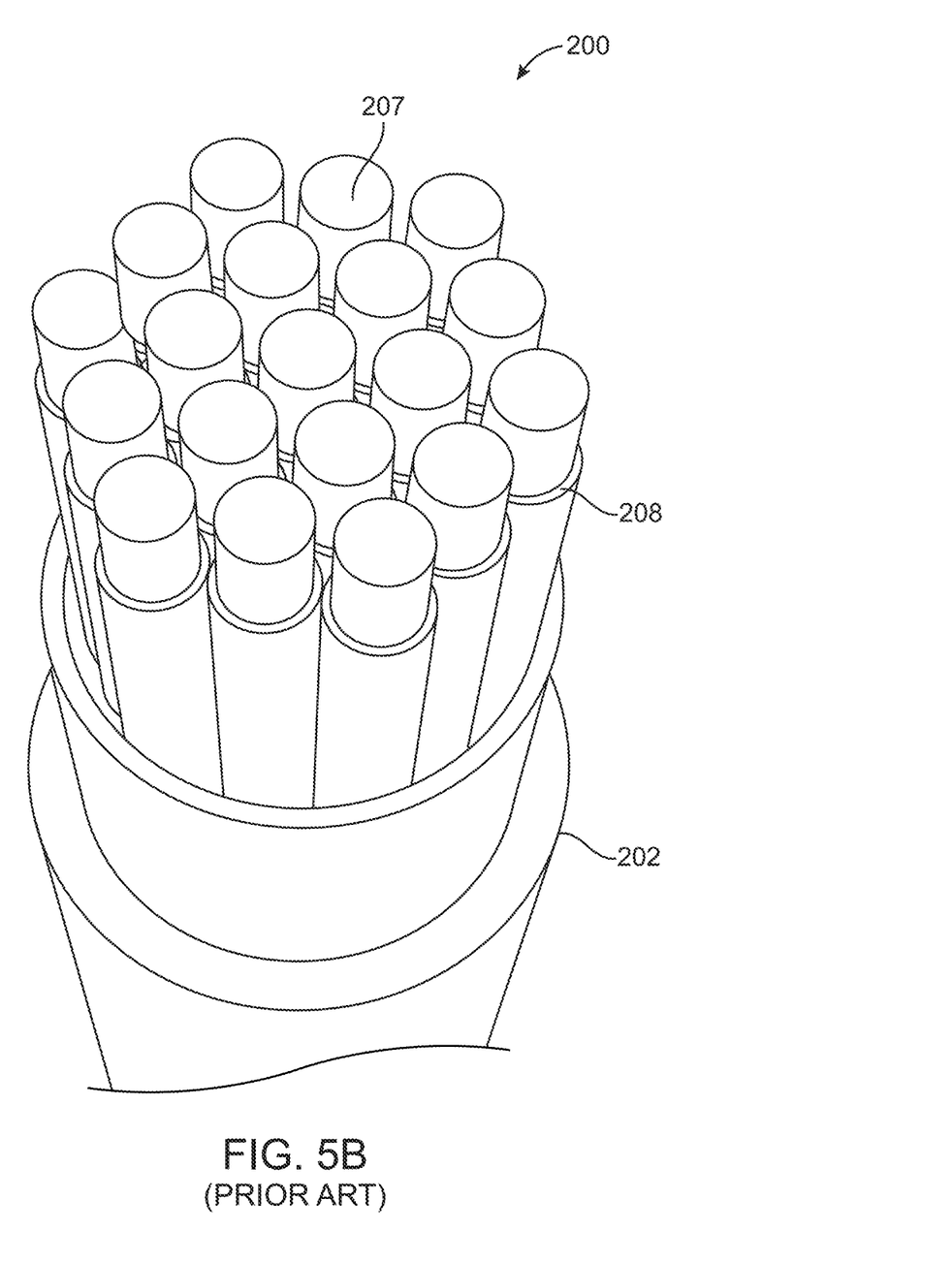
FIGS. 5B-5C illustrate conductors in a conventional Litz wire configuration.

FIG. 5A illustrates a cross-section of a conventional high strand conductor 302 including multiple bundles 308 of uninsulated wire strands 307 that are relatively tightly packed such that the increased friction between wire strands results in the presence of voids 309 between bundles. FIG. 5A illustrates a conductor having a 7×41/50 design, which is 7 bunches wrapped together, each bunch having 41 strands of 50 gauge wire for a total of 287 wire strands in the conductor. The increased voids increase the diameter of the cable and stresses in the wire strands when flexed as compared to cables having conductors in accordance with the present invention, such as that shown in FIG. 3.

As detailed above, a cable configuration in accordance with the invention includes conductors having bunches of loosely packed, uninsulated wire strands that may be wound or braided according to various winding patterns. In one aspect, the wire strands are wound according to three distinct winding patterns to form a triple-helix configuration. These winding patterns may correspond to winding or twisting patterns used in production of power cables, particularly those used in Litz wire production.

Figure 5C:
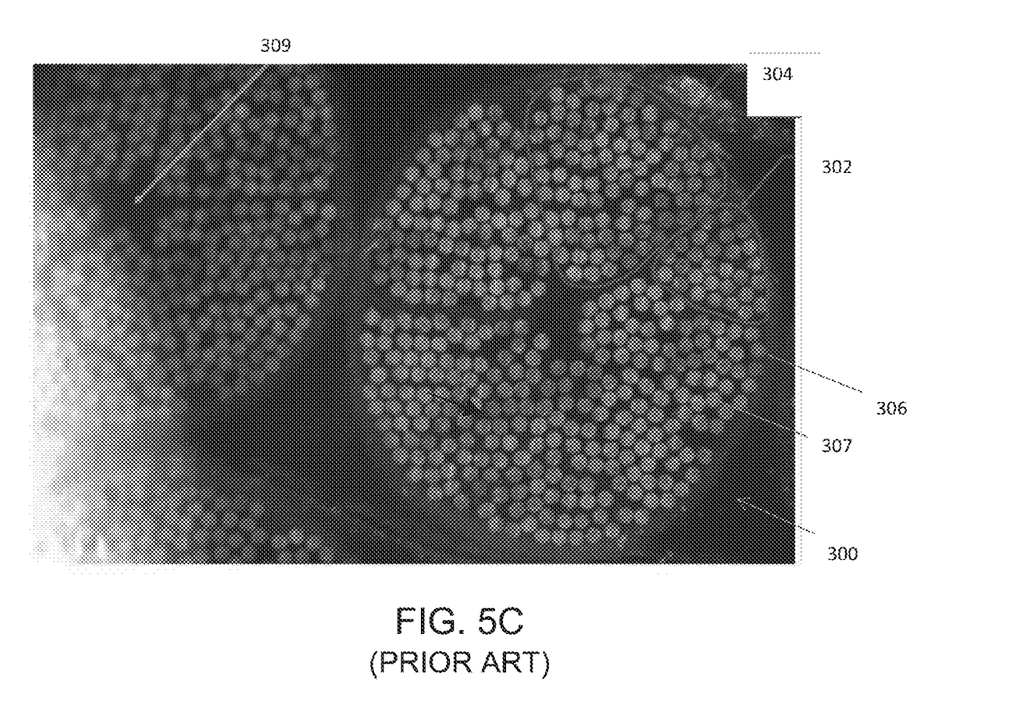

Litz wire conductors are configured for carrying AC specifically for high-frequency AC applications. The wire is designed to reduce the skin effect and proximity effect losses that occur in conductors used at frequencies up to about 1 MHz. A typical Litz wire conductor 200 consists of many thin wire strands 207 that are individually insulated 208, such as that shown in FIG. 5B. (Image found online at http://en.wikipedia.org/wiki/Litz_wire). The individually insulated wires are woven together according to one of various carefully prescribed patterns, such as shown in FIG. 4. (See images online at http://www.litzwire.com/litz-_types.htm). Such patterns/configurations typically involve several levels or steps so as to produce a winding pattern that equalizes the proportion of the overall length over which each wire strand is disposed toward the outside of the conductor. An example of a multiple winding pattern associated with a Litz wire style configuration is shown in FIG. 5C, which depicts an insulated conductor 300 having a 5×3×28/44 design. This design is formed by winding five bundles of 44 gauge wire (84 strands each) 304, each bundle formed by wrapping three bunches of wire strands together (28 strands each) 302, so as to form a conductor 306 having 420 total strands of 44 gauge wire wrapped in an insulative coating to form an insulated conductor 300. While this design includes loosely packed strands such that the overall voids are reduced. Although overall voids are reduced, occasionally small voids may still form, for example, the small star shaped void 309 formed at the center portion of the conductor shown at left.

For AC, the skin effect causes the resistance to increase with increasing frequency. For low frequencies, however, the effect is negligible such that there would be no apparent reason to utilize a Litz wire for such applications. For AC at frequencies sufficiently high such that the skin depth is small as compared to a size of the conductor, the skin effect causes much of the current to flow at or near the conductor's surface. At high enough frequencies, the center portion of a large conductor does not carry much current. Since conductors that are round and of a diameter larger than a few skin depths don't conduct much current near the center axis, when larger conductors are needed, Litz wires may be used to reduce the skin effect. By employing stranded wire that are individually insulated bundled conductors, each thin conductor of the inventive cable is less than a skin-depth such that there is no appreciable skin effect loss for each individual wire strand.

To provide this effect, each individual strand must be insulated from each other otherwise all the wires in the bundle would short together and behave much like a single larger wire in which appreciable skin effect problems would occur. The weaving and twisting of the individually insulated wire strands prevents the strands from occupying the same radial position within the bundle, since the electromagnetic effects that cause the skin effect would still disrupt conduction. The weaving or twisting pattern of the wires, such as those shown in FIG. 4, are designed so that the individual strands are on the outside of the bundle for a distance where electromagnetic field changes are smaller and the strand sees lower resistance and are inside the bundle for a distance where the electromagnetic field changes are stronger and resistance is higher. If each wire strand has comparable impedance, the current is distributed equally among every strand within the cable which allows the interior of the Litz wire to contribute the cable's conductivity. For these reasons, Litz wire is used in high-frequency AC applications where skin effect poses severe problems. While Litz wire is one kind of stranded wire, its particular design configuration and use is not one of avoiding wire breakage due to material failure, but rather to prevent the losses due to the skin effect and proximity described above. Additional details regarding Litz wire configurations and their associated application can be found in the following references: Terman, Frederick E., Radio Engineers' Handbook, McGraw-Hill, (1943); Litz Wire Types & Construction, New England Wire Technologies, 2005; Butterworth, S. "Effective Resistance of Inductance Coils at Radio Frequency", Wireless and Wireless Eng. 3: August 1926; and Sullivan, Charles R., "Optimal Choice for Number of Strands in a Litz-Wire Transformer Winding", IEEE Transactions on Power Electronics 14 (2): (March 1999); the entire contents of which are incorporated herein for all purposes.

In contrast to Litz wire conductors, a cable in accordance with aspects of the invention utilizes uninsulated wire strands, although the cable may be arranged or wound in a Litz wire style configuration. A Litz wire style configuration may be loosely similar to a configuration (e.g., twisting pattern, arrangement) utilized in Litz wire fabrication, however, it is appreciated that the cable is not limited to any particular Litz wire configuration, nor do the embodiments described herein correspond in pattern or arrangement to any particular known Litz wire configuration. Such a cable in accordance with aspects of the invention may be used in a direct current or low-frequency AC application, as opposed to the high frequency AC applications for which conventional Litz wire is suited. Litz wire style conductors do not appear to be used in low-frequency AC applications or DC applications, let alone in driveline cable applications for implantable pump systems. Providing uninsulated wire strands in a Litz-style configuration is counter-intuitive since the resulting cable would lack the benefits associated with Litz wire in regard to reducing skin effect and proximity effect losses. This configuration in which loosely packed uninsulated wire strands are utilized allows for various other advantages such as markedly improved durability at reduced cost of materials and manufacture and improved integrity of the electrical connection as compared to conventional driveline configurations as described herein.

Figure 6:
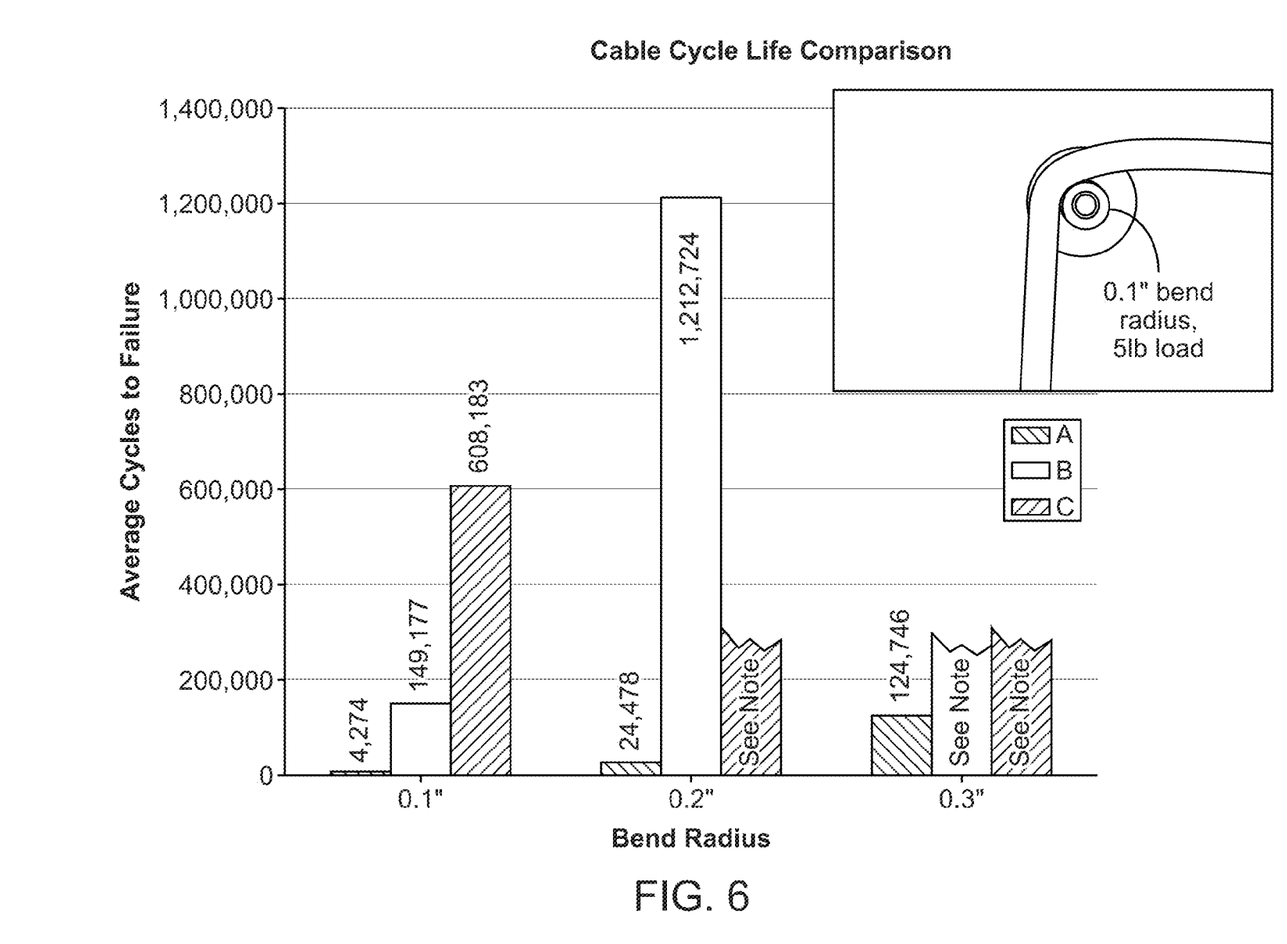
FIG. 6 is a graph depicting experimental results of cycle life of a cable configuration in accordance with aspects of the invention as compared to conventional cable configurations.

FIG. 6 illustrates experimental results demonstrating the durability of a driveline in accordance with aspects of the invention, cable configuration B (shown in FIG. 2), relative conventional driveline cables A and cable C (drawn-filled tube type cable, such as DFT®-drawn-filled tube—sold by Fort Wayne Metals Research Products Corp. of Fort Wayne, Ind. used here). The details of each of the cable configurations are shown in Table 1 below. As can be seen from the graph in FIG. 6, at a bend radius of 0.1", cable configuration B exhibits a cycle life of 149,177 cycles to failure, about 35 times greater than that of conventional driveline cable A (4,274 cycles to failure). At a bend radius of 0.2", the cycle life of cable configuration B is even higher at 1,212,724 cycles to failure, about 49 times higher than that of cable configuration A (24,478 cycles to failure). While cable configuration C using conductors of drawn-filled tube (DFT) exhibits durability greater than that of cable configuration B at 0.1" bend radius (and may do so at 0.2" and 0.3" as well), the costs of materials and production of drawn-fill tube are considerably greater than the costs of cable configuration B. At present, the cost of DFT is several orders of magnitude higher than Cd—Cu or Cu alloys. (Note: These tests were not run because the test duration is estimated to range between 70 to 700 days. The cycle tester has a max speed of 72,000 cycles per day). Since configurations A and B use similar materials, the costs of materials and production are on a similar scale such that the improvements in durability provided by the design configuration of cable configuration B represent allows for improved durability at substantially lower costs.

TABLE 1

Comparison of Example Driveline to Conventional Drivelines

| Item | A | C | B |
|---|---|---|---|
| 1 | Polyethylene strength member | | |
| 2 | Six insulated Cad-Copper conductors 65 strands per conductor 0.82 inch pitch | Six insulated DFT conductor 133 strands per conductor 1.00 inch pitch | Six insulated Cad-Copper conductors 288 strands per conductor 0.60 inch pitch |
| 3 | Copper braided shield | | PTFE Wrap |
| 4 | | Bionate | |
| 5 | Empty space | | Aramid Armor Layer |
| 6 | | Silicone Jacket | |

*Note:
the cables used to generate the data in FIG. 6 did not include items 5 and 6

Although the invention is described in terms of a driveline for a VAD, one will appreciate that the invention may be applied equally to other designs. For example, the invention may be applied to electronics, motors, batteries, antennas, and more.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A driveline cable for an implantable heart pump, the driveline cable comprising:

a plurality of conductors wound along a longitudinal axis of the cable, each conductor comprising a plurality of uninsulated wire strands disposed within an outer insulating layer, wherein the plurality of uninsulated wire strands in each conductor are loosely packed such that a majority of the uninsulated wire strands are movable relative other wire strands when the conductor is flexed, wherein the plurality of wire strands of each conductor are of a 30 gauge or higher and each conductor comprises a plurality of bunches of wire strands, each bunch having at least 32 wire strands of the plurality of wire strands; and an outer jacket disposed about the wound plurality of conductors.

2. The driveline cable of claim 1, wherein the plurality of strands of each conductor comprise a-plurality of uninsulated bundles of wire strands wound together in a first pattern along a longitudinal axis of the conductor.

3. The driveline cable of claim 2, wherein each bundle comprises a plurality of bunches of wire strands wound together in a second pattern along a longitudinal axis of the respective bundle.

4. The driveline cable of claim 3, wherein each bunch of wire strands comprises a group of wire strands wound together in a third pattern along a longitudinal axis of the respective bunch.

5. The driveline cable of claim 4, wherein the plurality of insulated conductors are wound in a fourth pattern along a longitudinal axis of the cable.

6. The driveline cable of claim 4, wherein the third pattern comprises a wrapping the conductors around a central core at a pitch of 0.75 inch or less along the longitudinal axis of the core.

7. The driveline cable of claim 4, wherein the first, second and third patterns correspond to those of a Litz wire winding configuration.

8. The driveline cable of claim 7, wherein the Litz wire winding configuration corresponds to a Type 5 Litz wire configuration.

9. The driveline cable of claim 4, wherein the plurality of wire strands of each conductor are wound in a 3×3×32 configuration.

10. The driveline cable of claim 1, wherein the plurality of wire strands of each conductor comprise a total of at least 200 wire strands.

11. The driveline cable of claim 1, wherein the plurality of wire strands of each conductor are strands of a copper alloy.

12. The driveline cable of claim 11, wherein the one or more conductors comprises 6 insulated conductors wrapped about a solid core of the cable, each conductor comprising 288 uninsulated copper strands.

13. A method of assembling a power cable for use with an implantable heart pump, the method comprising:
winding a plurality of uninsulated wire strands to form a plurality of bunches, the wire strands of each bunch being wound in a first pattern along a longitudinal axis of the respective bunch and being loosely packed such that a majority of the wire strands in each bunch are movable relative other wire strands of the bunch when the cable is flexed;
winding the plurality of bunches to form a plurality of bundles, each bundle comprising multiple bunches of wire strands wound in a second pattern along a longitudinal axis of the respective bundle;
winding the plurality of bundles to form a plurality of conductors, each conductor of the plurality comprising multiple bundles of wire strands wound in a third pattern along a longitudinal axis of the respective conductor;
winding the plurality of conductors together in a fourth pattern along a longitudinal axis of the power cable; and
covering the wound plurality of conductors with an outer insulating layer.

14. The method of claim 13, further comprising:
covering each of the plurality of conductors with an outer insulating layer before winding of the plurality of conductors together in the fourth pattern.

15. The method of claim 13, wherein the first, second and third winding patterns correspond to a Litz wire configuration.

16. The method of claim 13, wherein the plurality of conductors comprises at least six conductors wrapped around a central core of the cable.

17. The method of claim 16, wherein winding the conductors comprises wrapping the conductors together at a pitch of 0.75 inch or less along the longitudinal axis of the cable.

18. The method of claim 16, wherein each conductor comprises at least 200 wire strands of a copper alloy.

19. The method of claim 16, further comprising:
covering the wound conductors with a layer of PTFE.

20. The method of claim 19, further comprising:
covering the PTFE layer with a thermoplastic polycarbonate polyurethane, an aramid armor layer and a silicone jacket.

21. A method of powering a device for use with an implantable heart pump, the method comprising:
electrically connecting a power cable to the implantable heart pump, wherein the power cable comprises: a plurality of conductors, each conductor comprising a plurality of loosely packed uninsulated wire strands, the plurality of wire strands of each conductor comprise at least 60 wire strands of a 30 gauge or higher, and an outer jacket covering the plurality of conductors; and
powering the implantable heart pump using a low frequency alternating current or a direct current transmitted through the power cable.

22. The method of claim 21, wherein each conductor comprises a plurality of bundles of loosely packed uninsulated wire strands wound about a longitudinal axis of the respective conductor and the plurality of conductors are wound about a longitudinal axis of the cable.

23. The method of claim 22, wherein the plurality of strands, the plurality of bundles and the plurality of cables are wound in patterns corresponding to those of a Litz wire configuration.

24. The method of claim 21, wherein the low-frequency alternating current is less than about 20 kHz.

25. The method of claim 21, wherein electrically connecting comprises implanting the power cable between the implantable heart pump and an implantable controller.

26. A method of powering a device for use with an implantable heart pump, the method comprising:
electrically connecting a power cable to the implantable heart pump, wherein the power cable comprises: a plurality of conductors, each conductor comprising a plurality of loosely packed uninsulated wire strands, and an outer jacket covering the plurality of conductors; and
powering the implantable heart pump using a low frequency alternating current or a direct current transmitted through the power cable, wherein powering the implantable heart pump with the cable comprises conducting electrical current between adjacent uninsulated wire strands of the plurality of wire strands such that electrical transmission is maintained through each conductor including any conductor having broken wire strands of the plurality of wire strands.

* * * * *